United States Patent [19]

Baichwal

[11] Patent Number: 5,399,359
[45] Date of Patent: Mar. 21, 1995

[54] CONTROLLED RELEASE OXYBUTYNIN FORMULATIONS

[75] Inventor: Anand R. Baichwal, Wappingers Falls, N.Y.

[73] Assignee: Edward Mendell Co., Inc., Patterson, N.Y.

[21] Appl. No.: 206,416

[22] Filed: Mar. 4, 1994

[51] Int. Cl.⁶ ............................................. A61K 9/22
[52] U.S. Cl. .................................. 424/464; 424/468; 424/469; 424/484; 424/485; 424/488
[58] Field of Search ............... 424/464, 468, 469, 484, 424/485, 488

[56] References Cited

U.S. PATENT DOCUMENTS

| | | | |
|---|---|---|---|
| 4,303,691 | 12/1981 | Sand et al. | 426/573 |
| 4,792,452 | 12/1988 | Howard et al. | 424/475 |
| 4,795,642 | 1/1989 | Cohen et al. | 424/455 |
| 4,824,675 | 4/1989 | Wong et al. | 424/468 |
| 4,857,331 | 8/1989 | Shaw et al. | 424/484 |
| 4,886,669 | 12/1989 | Ventouras | 424/469 |
| 4,894,232 | 1/1990 | Reiil et al. | 424/485 |
| 4,942,040 | 7/1990 | Ragnarsson et al. | 424/486 |
| 4,968,508 | 11/1990 | Oren et al. | 424/468 |
| 5,032,406 | 7/1991 | Dansereau et al. | 424/464 |
| 5,047,244 | 9/1991 | Sandvordecker et al. | 424/435 |
| 5,128,143 | 7/1992 | Baichwal et al. | 424/464 |
| 5,135,757 | 8/1992 | Baichwal et al. | 424/465 |
| 5,169,639 | 12/1992 | Baichwal et al. | 424/468 |
| 5,271,943 | 12/1993 | Bogart et al. | 424/484 |
| 5,330,761 | 7/1994 | Baichwal | 424/469 |
| 5,330,763 | 7/1994 | Gole et al. | 424/484 |

OTHER PUBLICATIONS

CA 120:227001x.
CA 120:62297g.
Derwent On–Line Search.

*Primary Examiner*—Thurman K. Page
*Assistant Examiner*—Amy Hulina
*Attorney, Agent, or Firm*—Steinberg, Raskin & Davidson

[57] ABSTRACT

A solid oral sustained release oxybutynin formulation includes a sustained release matrix including a gelling agent, an inert pharmaceutical diluent, and a cationic cross-linking agent.

18 Claims, No Drawings

CONTROLLED RELEASE OXYBUTYNIN FORMULATIONS

BACKGROUND OF THE INVENTION

The advantages of controlled release products are well known in the pharmaceutical field and include the ability to maintain a desired blood level of a medicament over a comparatively longer period of time while increasing patient compliance by reducing the number of administrations necessary to achieve the same. These advantages have been attained by a wide variety of methods. For example, different hydrogels have been described for use in controlled release medicines, some of which are synthetic, but most of which are semi-synthetic or of natural origin. A few contain both synthetic and non-synthetic material. However, some of the systems require special process and production equipment, and in addition some of these systems are susceptible to variable drug release.

Oral controlled release delivery systems should ideally be adaptable so that release rates and profiles can be matched to physiological and chronotherapeutic requirements.

While many controlled and sustained release formulations are already known for a variety of pharmaceutically active agents, to date there have not been any commercially available controlled or sustained release formulations for the drug oxybutynin, which is an antispasmodic agent for treating neurogenic bladders in humans.

In the United States, oxybutynin is commercially available as the chloride salt as Ditropan ® (Marion Merrell Dow Inc.) in both a 5 milligram tablet and as a syrup (5 mg/5 ml), and is also available as Urotrol ® (Baker Norton Pharmaceuticals, Inc.) as a 5 milligram tablet. Those formulations are said to provide an onset of effect 30–60 minutes after oral administration, a peak effect 3–6 hours after administration, and a duration of effect ranging from 6–10 hours. The formulation is usually administered to adults two-three times daily. The maximum dosage is considered to be 5 mg administered four times daily.

Previously, a heterodisperse polysaccharide excipient system and controlled release oral solid dosage forms were described in our U.S. Pat. Nos. 4,994,276, 5,128,143, and 5,135,757. These systems are commercially available under the tradename TIMERx ™ from Edward Mendell Co., Inc., Patterson, N.Y., which is the assignee of the present invention. These patents are hereby incorporated by reference.

OBJECTS AND SUMMARY OF THE INVENTION

It is an object of the present invention to provide a sustained release formulation for the therapeutically active medicament commonly known as oxybutynin, and its pharmaceutically acceptable salts.

It is a further object of the present invention to provide a method for preparing a bioavailable sustained release formulation for oxybutynin.

The above-mentioned objects and others are achieved by virtue of the present invention, which relates in part to a solid sustained release oral dosage formulation comprising a therapeutically effective amount of oxybutynin or a pharmaceutically acceptable salt thereof, dispersed within a sustained release matrix comprising a gelling agent, an effective amount of a pharmaceutically acceptable water-soluble cationic cross-linking agent which cross-links with the gelling agent when the formulation is exposed to an environmental fluid, e.g., gastrointestinal fluid, and an inert diluent selected from, e.g., a monosaccharide, a disaccharide, a polyhydric alcohol, or mixtures thereof. The ratio of oxybutynin to gelling agent is preferably from about 1:3 to about 1:25, and more preferably from about 1:5 to about 1:15. The resulting tablet preferably provides a therapeutically effective blood level of the medicament for at least about 24 hours.

The present invention is also related to a method for providing a sustained release formulation for oxybutynin and/or its pharmaceutically acceptable salts, comprising preparing a sustained release matrix comprising from about 20 to about 60% by weight of a gelling agent, from about 1 to about 20% by weight of a cationic cross-linking agent, and from about 20% to about 79% by weight of an inert pharmaceutical diluent; adding an effective amount of oxybutynin to render a desired therapeutic effect, and thereafter tableting the resulting mixture such that a product is obtained having a ratio of oxybutynin to gelling agent from about 1:2 to about 1:25, preferably from about 1:5 to about 1:15, such that the resulting oral solid dosage form provides therapeutically effective blood levels of oxybutynin for at least about 24 hours.

The present invention is further related to a method of treating a patient by orally administering an oral solid dosage form (e.g., tablets, granules, pellets) as set forth above.

In preferred embodiments of the present invention, the gelling agent comprises a heteropolysaccharide gum and a homopolysaccharide gum capable of cross-linking said heteropolysaccharide gum when exposed to an environmental fluid.

By "sustained release" it is meant for purposes of the present invention that the therapeutically active medicament is released from the formulation at a controlled rate such that therapeutically beneficial blood levels (but below toxic levels) of the medicament are maintained over an extended period of time, e.g., providing a 24 hour dosage form.

By "bioavailable" it is meant for purposes of the present invention that the therapeutically active medicament is absorbed from the sustained release formulation and becomes available in the body at the intended site of drug action.

The term "environmental fluid" is meant for purposes of the present invention to encompass, e.g., an aqueous solution, or gastrointestinal fluid.

The term "oxybutynin" is meant for purposes of the present invention to encompass the free base of the drug and all of its pharmaceutically acceptable salts. However, all weight ratios expressed in this disclosure are based upon the chloride salt of oxybutynin.

DETAILED DESCRIPTION

Oxybutynin chloride (4-diethylamino-2-butynyl-phenylcyclohexylglycolate hydrochloride) directs antispasmodic effect on smooth muscle and inhibits the muscarinic action of acetylcholine on smooth muscle. No antinicotinic effects are known to exist with oxybutynin (e.g. no skeletal neuromuscular or autonomic ganglia blocking effects).

Therapeutically, oxybutynin is useful in the relief of symptoms of bladder instability associated with voiding of the bladder. Oxybutynin exerts its effect directly on the smooth muscle of the bladder and diminishes the frequency of uninhibited contractions of the detrusor muscle, delaying the initial desire to void.

The sustained release oral solid dosage forms of the present invention preferably contain from about 5 to about 20 mg oxybutynin, by weight (based on oxybutynin chloride). In a most preferred embodiment, the dosage form includes about 10 mg oxybutynin.

The gelling agent used in the present invention is preferably a heterodisperse gum comprising a heteropolysaccharide component and a homopolysaccharide component which exhibit synergism, e.g., the combination produces a higher viscosity and faster hydration than that which would be expected by either of the gums alone, the resultant gel being faster-forming and more rigid.

The term "heteropolysaccharide" as used in the present invention is defined as a water-soluble polysaccharide containing two or more kinds of sugar units, the heteropolysaccharide having a branched or helical configuration, and having excellent water-wicking properties and immense thickening properties.

An especially preferred heteropolysaccharide is xanthan gum, which is a high molecular weight ($>10^6$) heteropolysaccharide. Other preferred heteropolysaccharides include derivatives of xanthan gum, such as deacylated xanthan gum, the carboxymethyl ether, and the propylene glycol ester.

The homopolysaccharide gums used in the present invention which are capable of cross-linking with the heteropolysaccharide include the galactomannans, i.e., polysaccharides which are composed solely of mannose and galactose. Galactomannans which have higher proportions of unsubstituted mannose regions have been found to achieve more interaction with the heteropolysaccharide. Locust bean gum, which has a higher ratio of mannose to the galactose, is especially preferred as compared to other galactomannans such as guar and hydroxypropyl guar.

The sustained release properties of the oxybutynin formulations of the present invention may be optimized when the ratio of heteropolysaccharide gum to homopolysaccharide material is about 1:1, although a ratio of heteropolysaccharide gum to homopolysaccharide gum from about 1:3 to about 3:1 may be used in the formulations of the present invention.

The combination of xanthan gum with locust bean gum with or without the other homopolysaccharide gums is an especially preferred gelling agent. The chemistry of certain of the ingredients comprising the excipients of the present invention such as xanthan gum is such that the excipients are considered to be self-buffering agents which are substantially insensitive to the solubility of the medicament and likewise insensitive to the pH changes along the length of the gastrointestinal tract.

The inert diluent included in the sustained release matrix preferably comprises a pharmaceutically acceptable saccharide, including a monosaccharide, a disaccharide, or a polyhydric alcohol, and/or mixtures of any of the foregoing. Examples of suitable inert pharmaceutical fillers include sucrose, dextrose, lactose, microcrystalline cellulose, fructose, xylitol, sorbitol, mixtures thereof and the like. However, it is preferred that a soluble pharmaceutical filler such as lactose, dextrose, sucrose, or mixtures thereof be used.

The sustained release matrix includes a cationic cross-linking agent capable of cross-linking with the gelling agent. The cationic crosslinking agent is preferably included in an amount sufficient to significantly increase the gel strength of the formulation when it is exposed to an environmental (e.g., gastric) fluid, thereby preventing an initial "burst" of drug release from the formulation.

The cationic cross-linking agent may be monovalent or multivalent metal cations. The preferred salts are the inorganic salts, including various alkali metal and/or alkaline earth metal sulfates, chlorides, borates, bromides, citrates, acetates, lactates, etc. Specific examples of suitable cationic cross-linking agents include calcium sulfate, sodium chloride, potassium sulfate, sodium carbonate, lithium chloride, tripotassium phosphate, sodium borate, potassium bromide, potassium fluoride, sodium bicarbonate, calcium chloride, magnesium chloride, sodium citrate, sodium acetate, calcium lactate, magnesium sulfate and sodium fluoride. Multivalent metal cations may also be utilized. However, the preferred cationic cross-linking agents are bivalent. Particularly preferred salts are calcium sulfate and sodium chloride. The cationic cross-linking agents of the present invention are added in an amount effective to obtain a desirable increased gel strength due to the cross-linking of the gelling agent (e.g., the heteropolysaccharide and homopolysaccharide gums). In certain preferred embodiments, the cationic cross-linking agent is included in the sustained release matrix of the present invention in an amount from about 1 to about 20% by weight.

In preferred embodiments of the present invention, the sustained release matrix comprises from about 20% to about 60% of the gelling agent, from about 1 to about 20% by weight of a cationic cross-linking agent, and from about 20% to about 79% of the inert diluent, by weight. In more preferred embodiments, the sustained release matrix comprises from about 25 to about 50 percent gelling agent, from about 5 to about 15 percent cationic crosslinking agent, and from about 35 to about 70 percent inert diluent. In a most preferred embodiment, the sustained release matrix comprises from about 25 to about 35 percent gelling agent, from about 5 to about 15 percent cationic crosslinking agent, and from about 50 to about 70 percent inert diluent.

The sustained release matrix of the present invention may be further modified by incorporation of a hydrophobic material which slows the hydration of the gums without disrupting the hydrophilic matrix. This is accomplished in preferred embodiments of the present invention by granulating the sustained release excipient with the solution or dispersion of a hydrophobic material prior to the incorporation of the medicament. The hydrophobic polymer may be selected from an alkylcellulose such as ethylcellulose, other hydrophobic cellulosic materials, polymers or copolymers derived from acrylic or methacrylic acid esters, copolymers of acrylic and methacrylic acid esters, zein, waxes, shellac, hydrogenated vegetable oils, and any other pharmaceutically acceptable hydrophobic material known to those skilled in the art. The amount of hydrophobic material incorporated into the sustained release excipient is that which is effective to slow the hydration of the gums without disrupting the hydrophilic matrix formed upon exposure to an environmental fluid. In certain preferred embodiments of the present invention, the hydrophobic material is included in the sustained release excipient in an amount from about 1 to about 20 percent by weight, and replaces a corresponding amount of the inert diluent. The solvent for the hydrophobic material may be an aqueous or organic solvent, or mixtures thereof.

Examples of commercially available alkylcelluloses are Aquacoat ® (aqueous dispersion of ethylcellulose available from FMC) and Surelease ® (aqueous dispersion of ethylcellulose available from Colorcon). Examples of commercially available acrylic polymers suitable for use as the hydrophobic material include Eudragit ® RS and RL (copolymers of acrylic and methacrylic acid esters having a low content (e.g., 1:20 or 1:40) of quaternary ammonium compounds).

Once the sustained release excipient of the present invention has been prepared, it is then possible to blend the same with the oxybutynin, e.g., in a tumbling blender. The resultant mixture may then be directly compressed into tablets preferably after adding an effective amount of any generally accepted pharmaceutical lubricant, including the calcium or magnesium soaps. The lubricant may be added to the above-mentioned ingredients of the excipient be added at the time the medicament is added, or in any event prior to compression into a said dosage form. An example of a suitable lubricant is magnesium stearate in an amount of about 0.5 to about 3% by weight of the solid dosage form. An especially preferred lubricant is sodium stearyl fumarate, NF, commercially available under the trade name Pruv ® from the Edward Mendell Co., Inc.

The mixtures of oxybutynin and the sustained release matrixes of the present invention have uniform packing characteristics over a range of different particle size distributions and are capable of processing into the final dosage form (e.g., tablets) using either direct compression, following addition of drug and lubricant powder, or conventional wet granulation.

When the final product to be manufactured is tablets, the complete mixture, in an amount sufficient to make a uniform batch of tablets, is then subjected to tableting in a conventional production scale tableting machine at normal compression pressure, i.e. about 2000-1600 lbs/sq in. However, the mixture should not be compressed to such a degree that there is subsequent difficulty in its hydration when exposed to gastric fluid.

In further embodiments of the present invention, the sustained release matrix and oxybutynin are blended together with a further release rate modifying ingredient which is capable of slowing the release rate of the final product. In certain embodiments, this further ingredient comprises an effective amount of microcrystalline cellulose in an amount from about 1% to about 10% by weight of the final product. Alternatively, this further ingredient may be a hydrophobic material as set forth above with respect to the sustained release matrix. Generally, the amount of such release rate modifying ingredient is from about 1% to about 10% by weight of the final product.

In further embodiments, the dosage form, e.g., tablets, may be coated with a hydrophilic or hydrophobic coating. An example of a suitable material which may be used for such a hydrophilic coating is hydroxypropylmethyl-cellulose (e.g., Opadry ®, commercially available from Colorcon, West Point, Pa.). Examples of suitable hydrophobic coatings include ethylcellulose and/or acrylic polymers, as previously described.

The coatings may be applied in any pharmaceutically acceptable manner known to those skilled in the art. For example, in one embodiment, the coating is applied via a fluidized bed or in a coating pan. For example, the coated tablets may be dried, e.g., at about 60°-70° C. for about 3-4 hours in a coating pan. The solvent for the hydrophilic or hydrophobic polymer coating may be organic, aqueous, or a mixture of an organic and an aqueous solvent. The organic solvents may be, e.g., isopropyl alcohol, ethanol, and the like, with or without water. In such embodiments, an additional dose of the medicament may be included in the coating. This may be desired when, for example, a loading dose of a therapeutically active agent is needed to provide therapeutically effective blood levels of the active agent when the formulation is first exposed to gastric fluid. The loading dose of medicament included in the coating layer may be, e.g., from about 10% to about 40% of the total amount of medicament included in the formulation.

DETAILED DESCRIPTION OF THE PREFERRED EMBODIMENTS

The following examples illustrate various aspects of the present invention. They are not to be construed to limit the claims in any manner whatsoever.

EXAMPLES 1-2

Effect of Calcium Sulfate in Excipient

In Example 1-2, sustained release excipients in accordance with the present invention are first prepared, the medicament (in this case oxybutynin) being added subsequently, and the final mixture then being tableted.

The sustained release excipient is prepared by dry blending the requisite amounts of xanthan gum, locust bean gum, calcium sulfate, and dextrose in a high speed mixer/granulator for 2 minutes. While running choppers/impellers, the requisite amount of water is added to the dry blended mixture, and granulated for another 2 minutes. The granulation is then dried in a fluid bed dryer to a LOD (loss on drying) of less than about 10% by weight (e.g., 4-7% LOD). The granulation is then milled using 20 mesh screens. The ingredients of the granulations of Examples 1-2 are set forth in Table 1 below:

TABLE 1

| PREPARATION OF SUSTAINED-RELEASE EXCIPIENT | | |
|---|---|---|
| Component | % - Ex. 1 | % - Ex. 2 |
| 1. Xanthan Gum | 25 | 25 |
| 2. Locust Bean Gum | 25 | 25 |
| 3. Dextrose | 40 | 30 |
| 4. Calcium Sulfate | 10 | 20 |
| 5. Water | 10* | 10* |

*Removed during processing.

Next, the sustained-release excipient prepared as detailed above is dry blended with the desired amount of oxybutynin HCl in a V-blender for 10 minutes. A suitable tableting lubricant (Pruv ®, sodium stearyl fumarate, NF, commercially available from the Edward Mendell Co., Inc.) is added, and the mixture is blended for another 5 minutes. This final mixture is compressed into tablets. The ingredients of the tablets of Examples 1-2 are set forth in Table 2 below:

TABLE 2

| TABLET FORMULATION - EXAMPLES 1-2 | | |
|---|---|---|
| Component | % - Ex. 1 | % - Ex. 2 |
| 1. TIMERx ® | 93.8 | 93.8 |
| 2. Oxybutynin HCl | 4.7 | 4.7 |
| 3. Sodium stearyl fumarate | 1.5 | 1.5 |
| Tablet weight (mg) | 213.2 | 213.2 |

TABLE 2-continued

TABLET FORMULATION - EXAMPLES 1-2

| Component | % - Ex. 1 | % - Ex. 2 |
|---|---|---|
| Hardness (Kp) | 3.3 | 1.4 |

Dissolution tests were then carried out on the tablets of Examples 1-2. The dissolution tests are conducted in a pH 1.5 buffer in an automated USP dissolution apparatus (Paddle type II, 50 rpm), and the amount of drug released was analyzed via UV analysis or, alternatively by High Performance Liquid Chromatography (HPLC). The results are set forth in Table 3 below.

TABLE 3

Apparatus: Type II
Media: pH 1.5 buffer
Agitation: 50 rpm
Volume: 900 mL

| Time (hrs) | Ex. 1 | Ex. 2 |
|---|---|---|
| 0 | 0.0 | 0.0 |
| 2 | 38.6 | 37.8 |
| 4 | 64.2 | 51.2 |
| 8 | 88.9 | 84.7 |
| 12 | 96.8 | 95.4 |
| 16 | 100.3 | 98.1 |
| 20 | 100.8 | 97.7 |
| 24 | 101.0 | 94.8 |

From the results provided in Table 3, it is evident that addition of calcium sulfate produces slower drug release rates in the initial stages of dissolution. The reduction in release rate is made slower by a corresponding increase in the amount of calcium sulfate added to the formulation.

EXAMPLES 3-4

Effect of Drug:Gum Ratio

In Examples 3-4, a sustained release excipient is prepared in accordance with the procedures set forth for Examples 3-4. The ingredients of the sustained release matrix of Examples 4-5 are set forth in Table 4 below:

TABLE 4

| Component | % Ex. 3 | % Ex. 4 |
|---|---|---|
| 1. Xanthan Gum | 15 | 15 |
| 2. Locust bean Gum | 15 | 15 |
| 3. Dextrose | 60 | 60 |
| 4. Calcium Sulfate | 10 | 10 |
| 5. Water | 10* | 10* |

*Removed during processing.

Thereafter, oxybutynin tablets are prepared in accordance with the procedure set forth in Examples 1-2. The ingredients of the tablets of Examples 3-4 are forth in Table 5 below:

TABLE 5

| Component | % Ex. 3 | % Ex. 4 |
|---|---|---|
| 1. TIMERx ® | 95.7 | 93.0 |
| 2. Oxybutynin HCl | 2.9 | 5.6 |
| 3. Sodium stearyl fumarate | 1.4 | 1.4 |
| Tablet weight (mg) | 348.3 | 179.3 |
| Hardness (Kp) | 10.4 | 3.3 |

In Example 3, the drug:gum ratio is about 1:10. In Example 4, the drug:gum ratio is about 1:5. By "gum" it is meant the combined weight of xanthan gum and locust bean gum.

Tablets prepared in accordance with Examples 3-4 are then tested with regard to dissolution according to the procedure set forth with respect to Examples 1-2. The dissolution results for the Examples 3-4 are provided in Table 6 below.

TABLE 6

Apparatus: Type II
Media: pH 1.5 buffer
Agitation: 50 rpm
Volume: 900 mL

| Time (hrs) | Ex. 3 | Ex. 4 |
|---|---|---|
| 0 | 0.0 | 0.0 |
| 2 | 31.3 | 46.7 |
| 4 | 53.6 | 73.9 |
| 8 | 73.0 | 95.9 |
| 12 | 86.2 | 99.8 |
| 16 | 92.3 | 101.1 |
| 20 | 92.7 | 102.4 |
| 24 | 96.1 | 100.0 |

As can be seen from the results provided in Table 6, the rate of release of oxybutynin was slower as the amount of gum in the formulations is increased.

EXAMPLES 5-8

Effect of Microcrystalline Cellulose Addition

In Examples 5-8, a sustained release excipient is prepared in accordance with the procedures set forth for Examples 1-2. The ingredients of the sustained release excipient of Examples 5-8 are set forth in Table 7 below:

TABLE 7

| | Percent Included | | | |
|---|---|---|---|---|
| Component | Ex. 5 | Ex. 6 | Ex. 7 | Ex. 8 |
| 1. Xanthan Gum | 15 | 15 | 25 | 25 |
| 2. Locust Bean Gum | 15 | 15 | 25 | 25 |
| 3. Dextrose | 60 | 60 | 40 | 40 |
| 4. Calcium Sulfate | 10 | 10 | 10 | 10 |
| 5. Water | 10* | 10* | 10* | 10* |

*Removed during processing.

Thereafter, oxybutynin tablets are prepared according to the following method. The sustained-release excipient prepared as detailed above is dry blended with the requisite amounts of oxybutynin HCl, dextrose, and microcrystalline cellulose in a V-blender for 10 minutes. A suitable tableting lubricant (Pruv ®, sodium stearyl fumarate, NF, commercially available from Edward Mendell, Inc.) is added, and the mixture is blended for another 5 minutes. Then the mixture is compressed into tablets with the procedures set forth with respect to Examples 1-2. The final product has the following ingredients set forth in Table 8 below:

TABLE 8

| Component | Ex. 5 | Ex. 6 | Ex. 7 | Ex. 8 |
|---|---|---|---|---|
| 1. TIMERx ® | 90.9 | 88.3 | 89.1 | 53.0 |
| 2. Oxybutynin HCl | 2.7 | 5.3 | 4.5 | 5.3 |
| 3. Sodium stearyl fumarate | 1.4 | 1.4 | 1.4 | 0.9 |
| 4. Dextrose | — | — | — | 35.8 |
| 5. Microcrystalline cellulose | 5.0 | 5.0 | 5.0 | 5.0 |
| Tablet weight (mg) | 366.6 | 188.7 | 224.4 | 188.7 |
| Hardness (Kp) | 12.4 | 4.3 | 4.0 | 4.2 |

Tablets prepared in accordance with Examples 6-9 are then tested with regard to dissolution according to the procedure set forth with respect to Examples 1-2. The dissolution results for the Examples 5-8 are provided in Table 9.

TABLE 9

Apparatus: Type II
Media: pH 1.5 buffer
Agitation: 50 rpm
Volume: 900 mL

| Time (hours) | Ex. 5 | Ex. 6 | Ex. 7 | Ex. 8 |
|---|---|---|---|---|
| 0 | 0.0 | 0.0 | 0.0 | 0.0 |
| 2 | 38.4 | 48.1 | 38.7 | 45.0 |
| 4 | 59.6 | 79.0 | 55.6 | 70.2 |
| 8 | 84.2 | 102.6 | 78.7 | 94.6 |
| 12 | 93.9 | 105.7 | 90.3 | 92.1 |
| 16 | — | — | 97.2 | 104.8 |

As can be seen from the results provided in Table 9, the addition of microcrystalline cellulose as about 5% by weight of the formulation results in a slight reduction of the release rate of oxybutynin, and a slight increase in compressibility of the blend (resulting in harder tablets).

EXAMPLE 9

Effect of Ethylcellulose Addition

In Example 9, a sustained-release excipient is prepared in accordance with the following procedures. The requisite amount of ethylcellulose is dissolved in the ethyl alcohol. Xanthan gum, locust bean gum, dextrose and calcium sulfate are mixed in a high speed mixer/granulator for 2 minutes while running choppers/impellers, the ethylcellulose-ethyl alcohol solution is added to the dry blended mix and the mixture is granulated for another 2 minutes. The granulation is dried on a fluid bed dryer to a Loss on Drying (LOD) of less than about 10% (e.g., 4-7%). The dried granulation is milled through a 20 mesh screen. The ingredients of the sustained release excipient of Example 9 and Comparative Example 9A (no ethylcellulose included) are set forth in Table 10 below:

TABLE 10

| Component | % Ex. 9A | % Ex. 9 |
|---|---|---|
| 1. Xanthan Gum | 25 | 25 |
| 2. Locust Bean Gum | 25 | 25 |
| 3. Dextrose | 40 | 35 |
| 4. Calcium Sulfate | 10 | 10 |
| 5. Ethylcellulose | — | 5 |
| 6. Ethyl Alcohol | 10* | 20* |

*Removed during processing.

Thereafter, oxybutynin tablets are prepared in accordance with the procedures set forth with respect to Examples 1-2. The ingredients for the tablets of Example 9 and 9A are set forth in Table 11 below.

TABLE 11

| Component | % Ex. 9 | % Ex. 9A |
|---|---|---|
| 1. TIMERx ® | 95.3 | 95.3 |
| 2. Oxybutynin HCl | 3.2 | 3.2 |
| 3. Sodium stearyl fumarate | 1.5 | 1.5 |
| Tablet weight (mg) | 314.7 | 314.7 |
| Hardness (Kp) | 7.0 | 7.5 |

Tablets prepared in accordance with Examples 10 and 10A are then tested with regard to dissolution according to the procedure set forth with respect to Examples 1-2. The dissolution results for Examples 9 and 9A are provided in Table 12.

TABLE 12

Apparatus: Type II
Media: pH 1.5 buffer
Agitation: 50 rpm
Volume: 900 mL

| Time (hr) | Ex. 10 | Ex. 10A |
|---|---|---|
| 0 | 0.0 | 0.0 |
| 2 | 32.7 | 34.9 |
| 4 | 50.2 | 54.0 |
| 8 | 72.7 | 78.4 |
| 12 | 86.2 | 90.0 |
| 16 | 95.2 | 97.6 |
| 20 | 98.2 | 99.8 |
| 24 | 100.4 | 100.0 |

The addition of ethylcellulose in an amount of about 5% by weight of the formulation resulted in an increase of the release rate of oxybutynin.

EXAMPLES 10-13

Effect of Processing

In Examples 10-13, a sustained release excipient is prepared in accordance with the procedures set forth for Examples 1-2. The ingredients of the sustained release excipient of Examples 10-13 are set forth in Table 13 below:

TABLE 13

| Component | Ex. 10 | Ex. 11 | Ex. 12 | Ex. 13 |
|---|---|---|---|---|
| 1. Xanthan Gum | 15 | 15 | 25 | 25 |
| 2. Locust Bean Gum | 15 | 15 | 25 | 25 |
| 3. Dextrose | 60 | 60 | 40 | 40 |
| 4. Calcium Sulfate | 10 | 10 | 10 | 10 |
| 5. Water | 10* | 10* | 10* | 10* |

*Removed during processing.

Formulations were prepared according to two different procedures. In Examples 10 and 12, the sustained release matrix and drug were dry-blended. In Examples 11 and 13, the sustained release matrix and drug are wet granulated.

PROCEDURE ONE—EXAMPLES 10 AND 12

The sustained-release matrix as prepared above and the oxybutynin HCl are dry blended in a V-blender for 10 minutes. Sodium stearyl fumarate is then added, and the mixture is dry blended for another 5 minutes. The blended mixture is then compressed into tablets.

PROCEDURE TWO—EXAMPLES 11 AND 13

The sustained-release carrier as prepared above and the oxybutynin HCl are blended in a high speed mixer/granulator for 2 minutes. While running choppers/impellers, the requisite amount of water is added to the mixture. The mixture is then granulated for another 2 minutes. The resultant granulation is dried in a fluid bed dryer to a loss on drying of about 10% (e.g. 4-7% LOD). The dried granulation is then milled through a 20 mesh screen. Sodium stearyl fumarate is added to the milled granulation and the mixture is blended for 5 minutes in a V-blender. The resultant formulation is then compressed into tablets.

The ingredients of the tablets of Examples 10-13 are set forth in Table 14 below:

TABLE 14

| Component | Ex. 10 | Ex. 11 | Ex. 12 | Ex. 13 |
|---|---|---|---|---|
| 1. TIMERx ® | 95.6 | 95.6 | 93.8 | 93.8 |
| 2. Oxybutynin HCl | 2.9 | 2.9 | 4.7 | 4.7 |
| 3. Sodium stearyl fumarate | 1.5 | 1.5 | 1.5 | 1.5 |

TABLE 14-continued

| Component | Ex. 10 | Ex. 11 | Ex. 12 | Ex. 13 |
|---|---|---|---|---|
| 5. Water | 10* | 10* | 10* | 10* |
| Tablet weight (mg) | 348.3 | 348.5 | 213.2 | 213.2 |
| Hardness (Kp) | 10.4 | 9.9 | 3.3 | 5.4 |

*Removed during processing.

Tablets prepared in accordance with Examples 10–13 are then tested with regard to dissolution according to the procedure set forth with respect to Examples 1–2. The dissolution results for the Examples 10–13 are provided in Table 15.

TABLE 15

Apparatus: Type II
Media: pH 1.5 buffer
Agitation: 50 rpm
Volume: 900 mL

| Time (hours) | (DC)* Ex. 10 | (WG)** Ex. 11 | (DC)* Ex. 12 | (WG)** Ex. 13 |
|---|---|---|---|---|
| 0 | 0.0 | 0.0 | 0.0 | 0.0 |
| 2 | 31.3 | 35.6 | 38.6 | 36.1 |
| 4 | 53.6 | 55.5 | 64.2 | 53.5 |
| 8 | 73.0 | 81.1 | 88.9 | 76.8 |
| 12 | 86.2 | 94.5 | 96.8 | 89.8 |
| 16 | 92.3 | 98.5 | 100.3 | 96.0 |
| 20 | 92.7 | 99.1 | 100.8 | 98.8 |
| 24 | 96.1 | 98.5 | 101.0 | 95.0 |

*(DG) = Direct compression
**(WG) = Wet granulation

As can be seen from the results in Table 15, for a sustained release matrix having a 3:6 gum:sugar ratio, processing by wet granulation, rather than by direct compression, results in a slightly faster release rate of oxybutynin. For a sustained release matrix having a 5:4 gum:sugar ratio, processing by wet granulation, rather than by direct compression, results in a slower rate of release of oxybutynin.

EXAMPLES 14–15

Effect of Tablet Size

In Examples 14 and 15 a sustained release excipient is prepared in accordance with the procedures set forth for Examples 1–2. The ingredients of the sustained release excipient of Examples 14 and 15 are set forth in Table 16 below:

TABLE 16

| Component | % Ex. 14 | % Ex. 15 |
|---|---|---|
| 1. Xanthan Gum | 25 | 25 |
| 2. Locust Bean Gum | 25 | 25 |
| 3. Dextrose | 50 | 50 |
| 4. Water | 10* | 10* |

*Removed during processing.

Thereafter, oxybutynin tablets are prepared in accordance with the procedures set forth with respect to Examples 1–2. The dried granulation is tableted. The ingredients for the tablets of Examples 14 and 15 are set forth in Table 17 below:

TABLE 17

| Component | % Ex. 14 | % Ex. 15 |
|---|---|---|
| 1. TIMERx ® | 95.3 | 96.1 |
| 2. Oxybutynin HCl | 3.2 | 2.4 |
| 3. Sodium stearyl fumarate | 1.5 | 1.5 |
| Tablet weight (mg) | 314.7 | 416.2 |
| Hardness (Kp) | 1.7 | 3.2 |

Tablets prepared in accordance with Examples 16 and 17 are then tested with regard to dissolution according to the procedure set forth with respect to Examples 1–2. The dissolution results for the Examples 14 and 15 are provided in Table 18.

TABLE 18

Apparatus: Type II
Media: pH change method
Agitation: 50 rpm
Volume: 900 mL

| Time (hr) | Ex. 14 | Ex. 15 |
|---|---|---|
| 0 | 0.0 | 0.0 |
| 2 | 38.7 | 32.5 |
| 4 | 62.1 | 48.2 |
| 8 | 84.9 | 67.2 |
| 12 | 94.8 | 79.0 |
| 16 | 98.1 | 85.9 |
| 20 | 98.6 | 89.4 |
| 24 | 98.1 | 91.2 |

As can be seen from the results in Table 18, for similar formulations, as the tablet weight increases, release rate decreases.

The examples provided above are not meant to be exclusive. Many other variations of the present invention would be obvious to those skilled in the art, and are contemplated to be within the scope of the appended claims.

What is claimed is:

1. A sustained release tablet, comprising:
an effective amount of oxybutynin or a pharmaceutically acceptable salt thereof to provide an antispasmodic effect;
a sustained release matrix comprising from about 20 to about 60% by weight of a gelling agent comprising a heteropolysaccharide gum and a homopolysaccharide gum capable of cross-linking said heteropolysaccharide gum when exposed to an environmental fluid, the ratio of said heteropolysaccharide gum to said homopolysaccharide gum being from about 1:3 to about 3:1; an effective amount of a pharmaceutically acceptable cationic cross-linking agent selected from the group consisting of alkali metal and alkaline earth metal sulfates, chlorides, borates, bromides, citrates, acetates, lactates and mixtures thereof, capable of crosslinking with said gelling agent and increasing the gel strength when the dosage form is exposed to an environmental fluid; and an inert pharmaceutical diluent selected from the group consisting of monosaccharide, a disaccharide, a polyhydric alcohol, and mixtures thereof, the ratio of said oxybutynin to said gelling agent being from about 1:2 to about 1:25; said dosage form providing a sustained release of said oxybutynin when exposed to an environmental fluid.

2. The oral solid dosage form of claim 1, wherein the ratio of said oxybutynin to said gelling agent is from about 1:5 to about 1:15, by weight.

3. The oral solid dosage form of claim 1, wherein said heteropolysaccharide gum comprises xanthan gum and said homopolysaccharide gum comprises locust bean gum.

4. The oral solid dosage form of claim 1, wherein said cationic cross-linking agent comprises calcium sulfate.

5. The oral solid dosage form of claim 1, wherein said sustained release matrix further comprises a hydrophobic material selected from the group consisting of an alkylcellulose, a copolymer of acrylic and methacrylic acid esters, waxes, shellac, zein, hydrogenated vegetable oil, and mixtures thereof, in an amount effective to slow the hydration of said gelling agent when exposed to an environmental fluid.

6. The oral solid dosage form of claim 5, wherein said hydrophobic material is ethylcellulose.

7. The oral solid dosage form of claim 5, wherein said sustained release matrix comprises from about 1 to about 20% by weight of said hydrophobic material.

8. The oral solid dosage form of claim 1, further comprising from about 1 to about 10% by weight microcrystalline cellulose.

9. The oral solid dosage form of claim 1, wherein said oxybutynin is included in an amount from about 5 to about 20 mg.

10. The oral solid dosage form of claim 1, wherein said sustained release matrix comprises 20% to about 60% of the gelling agent, from about 1 to about 20% by weight of the cationic cross-linking agent, and from about 20% to about 79% of the inert diluent, by weight.

11. The oral solid dosage form of claim 1, wherein said sustained release matrix comprises from about 25 to about 50 percent gelling agent, from about 5 to about 15 percent cationic crosslinking agent, and from about 35 to about 70 percent inert diluent, by weight.

12. The oral solid dosage form of claim 1, wherein said sustained release matrix comprises from about 25 to about 35 percent gelling agent, from about 5 to about 15 percent cationic crosslinking agent, and from about 50 to about 70 percent inert diluent, by weight.

13. The oral solid dosage form of claim 1, which provides effective blood levels of oxybutynin for about 24 hours when orally administered to a human patient.

14. A method of preparing a solid oral sustained release formulation of oxybutynin, comprising:
preparing a sustained release matrix comprising from about 20 to about 60 percent by weight of a gelling agent comprising a heteropolysaccharide gum and a homopolysaccharide gum capable of cross-linking said heteropolysaccharide gum when exposed to an environmental fluid, the ratio of said heteropolysaccharide gum to said homopolysaccharide gum being from about 1:3 to about 3:1, a cationic crosslinking agent selected from the group consisting of alkali metal and alkaline earth metal sulfates, chlorides, borates, bromides, citrates, acetates, lactates and mixtures thereof, in an amount effective to crosslink with said gelling agent and increase the gel strength when exposed to an environmental fluid, and an inert diluent,
mixing said sustained release matrix with oxybutynin or a pharmaceutically acceptable salt thereof, such that the ratio of oxybutynin to gelling agent is from about 1:2 to about 1:25 by weight, and
compressing said mixture of sustained release matrix and oxybutynin into tablets having an amount of oxybutynin necessary to render an antispasmodic effect, said tablets providing a sustained release of oxybutynin for about 24 hours when exposed to an environmental fluid.

15. The method of claim 14, further comprising including in said sustained release excipient from about 1 to about 20 percent by weight of said cationic crosslinking agent.

16. The method of claim 15, further comprising granulating said sustained release excipient with a hydrophobic material.

17. The method of claim 15, wherein said cationic cross-linking agent is calcium sulfate and said hydrophobic coating comprises ethylcellulose.

18. A method of treating a patient with oxybutynin, comprising
preparing a sustained release matrix comprising from about 20 to about 60 percent by weight of a gelling agent comprising a heteropolysaccharide gum and a homopolysaccharide gum capable of cross-linking said heteropolysaccharide gum when exposed to an environmental fluid, the ratio of said heteropolysaccharide gum to said homopolysaccharide gum being from about 1:3 to about 3:1, a cationic crosslinking agent selected from the group consisting of alkali metal and alkaline earth metal sulfates, chlorides, borates, bromides, citrates, acetates, lactates and mixtures thereof, in an amount effective to crosslink with said gelling agent and increase the gel strength of the formulation when it is exposed to gastrointestinal fluid, and an inert diluent,
mixing said sustained release matrix with oxybutynin or a pharmaceutically acceptable salt thereof, such that the ratio of oxybutynin to gelling agent is from about 1:2 to about 1:25 by weight,
compressing said mixture of sustained release matrix and oxybutynin into tablets having an amount of oxybutynin necessary to render an antispasmodic effect, said tablets providing a sustained release of oxybutynin for about 24 hours when exposed to gastrointestinal fluid, and
administering said tablets to a human patient in 24 hour intervals.

* * * * *